US008425490B2

(12) United States Patent
Ariza

(10) Patent No.: US 8,425,490 B2
(45) Date of Patent: Apr. 23, 2013

(54) DYNAMIC LIPOSCULPTING METHOD

(76) Inventor: Alfredo Ernesto Hoyos Ariza, Miami, FL (US)

( * ) Notice: Subject to any disclaimer, the term of this patent is extended or adjusted under 35 U.S.C. 154(b) by 91 days.

(21) Appl. No.: 13/171,025

(22) Filed: Jun. 28, 2011

(65) Prior Publication Data

US 2013/0006224 A1 Jan. 3, 2013

(51) Int. Cl.
*A61M 1/00* (2006.01)
(52) U.S. Cl.
USPC ............................ 604/542; 604/35; 128/898
(58) Field of Classification Search .................. 604/542, 604/35
See application file for complete search history.

(56) References Cited

U.S. PATENT DOCUMENTS

| 4,402,373 | A |   | 9/1983  | Comeau           |
|-----------|---|---|---------|------------------|
| 4,562,842 | A |   | 1/1986  | Morfeld et al.   |
| 4,676,780 | A | * | 6/1987  | Lee ............................. 604/117 |
| 4,923,461 | A |   | 5/1990  | Caspari et al.   |
| 4,935,027 | A |   | 6/1990  | Yoon             |
| 5,029,584 | A |   | 7/1991  | Smith            |
| 5,053,047 | A |   | 10/1991 | Yoon             |
| 5,181,907 | A |   | 1/1993  | Becker           |
| 5,222,976 | A |   | 6/1993  | Yoon             |
| 5,226,313 | A |   | 7/1993  | Murata et al.    |
| 5,236,664 | A |   | 8/1993  | Ludvigsen        |
| 5,255,669 | A |   | 10/1993 | Kubota et al.    |
| 5,275,613 | A |   | 1/1994  | Haber et al.     |
| 5,329,943 | A |   | 7/1994  | Johnson          |
| 5,330,503 | A |   | 7/1994  | Yoon             |
| 5,397,325 | A |   | 3/1995  | Della Badia et al. |
| 5,419,761 | A |   | 5/1995  | Narayanan et al. |
| 5,492,537 | A |   | 2/1996  | Vancaillie       |
| 5,643,198 | A |   | 7/1997  | Cucin            |
| 5,658,328 | A | * | 8/1997  | Johnson ............................. 623/8 |
| 5,683,366 | A |   | 11/1997 | Eggers et al.    |
| 5,884,631 | A |   | 3/1999  | Silberg          |
| 5,935,143 | A |   | 8/1999  | Hood             |
| 5,956,130 | A |   | 9/1999  | Vancaillie et al. |
| 6,071,260 | A |   | 6/2000  | Halverson        |
| 6,450,975 | B1 |  | 9/2002  | Brennan et al.   |
| 6,461,350 | B1 |  | 10/2002 | Underwood et al. |
| 6,524,250 | B1 | * | 2/2003 | Weber et al. .................. 600/439 |

(Continued)

OTHER PUBLICATIONS

Hoyos et al., VASER-Assisted High-Definition Liposculpture, Aesthetic Surgery Journal, 2007, 27:594-604 (Nov./Dec. 2007).

(Continued)

*Primary Examiner* — Melanie Hand
*Assistant Examiner* — Paula Craig
(74) *Attorney, Agent, or Firm* — Malloy & Malloy, P.L.

(57) ABSTRACT

A method of liposculpting a predetermined body area which is adjacently associated with at least one muscle bundle resulting in a natural, defined appearance of the muscle bundle. A treatment area from which fat tissue is removed by suction is at least partially defined by determining positions of the muscle in at least a relaxed state and a flexed or contracted state. Dependent on the particular physical characteristics of the affected muscle bundle, the flexed state can be defined by an isometric contraction as well as an isotonic contraction of the associated muscle bundle. The naturally defined appearance is accomplished by removing variable quantities of fat tissue from different portions of the treatment area, to the extent that greater quantity of fat tissue remains within the treatment area in a direction towards the substantial center of the muscle bundle and a gradually, successively lesser quantity of fat tissue remains within the treatment area in a direction away from the muscle bundle.

21 Claims, 4 Drawing Sheets

U.S. PATENT DOCUMENTS

| | | |
|---|---|---|
| 6,663,633 B1 | 12/2003 | Pierson, III |
| 6,920,883 B2 | 7/2005 | Bessette et al. |
| 6,986,776 B2 | 1/2006 | Craig |
| 7,331,951 B2 | 2/2008 | Eshel et al. |
| 7,637,918 B2 | 12/2009 | Dant |
| 7,857,773 B2 | 12/2010 | Desilets et al. |
| 8,167,868 B1* | 5/2012 | Ariza ............................ 604/542 |
| 2007/0060989 A1 | 3/2007 | Deem et al. |
| 2008/0195036 A1 | 8/2008 | Merchant et al. |
| 2009/0248004 A1 | 10/2009 | Altshuler et al. |
| 2010/0057056 A1* | 3/2010 | Gurtner et al. ................ 604/542 |
| 2010/0137256 A1* | 6/2010 | Haddad ......................... 514/114 |
| 2011/0144729 A1* | 6/2011 | Weber .............................. 607/99 |
| 2012/0265072 A1* | 10/2012 | Matlock ......................... 600/439 |

OTHER PUBLICATIONS

Gasperoni et al, Rationale of Subdermal Superficial Liposuction Related to the Anatomy of Subcutaneous Fat and the Superficial Fascial System, Aesthetic Plastic Surgery 19:13-20, 1995.

Avelar, Regional Distribution and Behavior of the Subcutaneous Tissue Concerning Selection and Indication for Liposuction, Aesthetic Plastic Surgery 13:155-165 (1989).

Fischer, Chapter 22: Liposculpture of the Trunk, Liposuction Principles and Practice, Springer-Verlag Berling Heidelberg, 2006.

Pitanguy et al., Chapter 23: Liposuction and Dermolipectomy, Liposuction Principles and Practice, Springer-Verlag Berling Heidelber, 2006.

de la Torre et al., Chapter 24: The Modern Lipoabdominoplasty, Liposuction Principles and Practice, Springer-Verlag Berling Heidelberg, 2006.

Raskin, Chapter 25: Abdominal Liposuction in Colostomy Patients, Liposuction Principles and Practice, Springer-Verlag Berling Heidelberg, 2006.

Raskin et al., Chapter 27: Microcannula Liposuction, Liposuction Principles and Practice, Springer-Verlag Berling Heidelberg, 2006.

Gasparotti, Chapter 29: Three-Dimensional Superficial Liposculpture for Aged and Relaxed Skin, Liposuction Principles and Practice, Springer-Verlag Berling Heidelberg, 2006.

Cimino, Chapter 34: VASER-Assisted Lipoplasty: Technology and Technique, Liposuction Principles and Practice, Springer-Verlag Berling Heidelberg, 2006.

Giuseppe, Alberto Di., Chapter 35: Ultrasound-Assisted Lipoplasty for Face Contouring with Vaser, Liposuction Principles and Practice, Springer-Verlag Berling Heidelberg, 2006.

Cimino, William W., Chapter 32: Ultrasound-Assisted Liposuction: Past, Present, and Future, Liposuction Principles and Practice, Springer-Veriag Berling Heidelberg, 2006.

\* cited by examiner

DYNAMIC LIPOSCULPTING METHOD

BACKGROUND OF THE INVENTION

1. Field of the Invention

This invention is directed to a method of performing a liposuction procedure resulting in a naturally defined area of a predetermined muscle bundle(s) resulting in an improved liposculpting technique. The treatment area from which fat tissue is removed by suction is determined by the positions of at least a portion of the associated muscle bundle when in a relaxed state and a contracted or flexed state. Thereafter, variable quantities of fat tissue are removed from different portions of the treatment area in order to better accentuate the appearance of the associated muscle bundle when in both the relaxed and contracted states.

2. Description of the Related Art

Liposuction is a surgical procedure which was introduced into the United States approximately thirty years ago. As such, the liposuction procedure is a common method for removing subcutaneous fat in order to achieve a more desirable and acceptable appearance of the body. Specifically, liposuction has been used in situations where conventional exercise and/or dieting has not been effective. It is generally recognized that liposuction surgery can be done safely and effectively in the removal of the subcutaneous fat deposits located relatively deep with respect to the under surface of the skin.

In accomplishing such fat removal and in performing the liposuction procedure, relatively blunt instruments are used. Such instruments are connected in fluid communication with a source of negative pressure or suction. The conventional use of such instrumentation and high pressure vacuum source accomplishes a generally random removal of fat tissue from the affected area. As a result, the overall appearance of the body area and that of the individual is dependent upon the judgment and skill of the medical personnel involved. Misjudgment occurring during the performance of such a procedure may result in a substantially abnormal, unnatural appearance. Accordingly, even with highly skilled surgeons variations in appearance of the body area and the overall body shape of the patient may vary significantly. Assuming the possibility of complications, unsuccessful results may be demonstrated by uneven or "lumpy" skin areas and an absence of definition of associated muscle groupings. In addition, safety factors must be seriously considered, due to the fact that a liposuction procedure may result in traumatized tissue, substantial blood loss, severe swelling and extensive post operative bruising. All of these occurrences extend the healing period and discomfort which the patient must endure.

In recent years the liposuction procedure has been improved to the extent that an experienced surgeon, utilizing appropriate instrumentation, can provide a more "sculpted" appearance resulting in improved body contour and muscle definition with minimal pain and scarring. As a result, liposuction procedures have more recently been sometimes referred to as "liposculpture". Accordingly it should be apparent, that an individual or patient undergoing the liposuction procedure hopes for removal of an appropriate amount body fat from certain areas of the body in a manner which leaves the patient with a more natural appearance, specifically but not exclusively, in the area from which fat tissue has been removed. Accordingly, an effective "liposculpture" procedure facilitates the defining of predetermined muscle groupings resulting in the individual having a "sculpted" appearance rather than just a body contour which appears to be reduced in overall bulk.

Therefore, there is a need in the area of "liposculpting" for a procedure and method which assuredly accomplishes a more defined appearance of any of a variety of different muscle groupings or muscle bundles. Such a proposed improvement should provide the patient with an appearance represented by clearly defined muscle bundles at the treated areas of the body including, but not limited to, muscles of the arms, legs, buttocks, abdomen, etc. In applying such an improved liposculpting method, medical personnel will be able to accomplish a more precise defining of the treatment area from which fat tissue is to be removed. The treatment area may be accurately determined by recognizing that the appearance of the treated individual will be observed while the affected muscle bundles are in both a relaxed state and a contracted or flexed state.

As a result, the improved method of liposculpting should consider removal of selective, rather than random, quantities of fat tissue from different portions of the treatment area. Such selective and variable fat tissue removal will serve to better accomplish the naturally defined and highly desirable appearance of the associated muscle grouping or groupings. Specifically, an improved method of liposculpting should include the variable quantities of fat tissue being removed from the treatment area to include and result in a greater quantity of fat remaining within the treatment area in a direction towards the substantial center of the associated muscle bundle(s). Such a variable quantity of fat tissue removable may be further defined by a gradual and successively lesser quantity of fat tissue remaining within the treatment area in a direction extending away from the center of the muscle bundle(s).

Practice of the proposed and practice surgical procedure results in a liposculpting method which accomplishes a clear and specific definition of associated muscle bundles when either the relaxed state or in various states of contraction. As such, it should be recognized that certain muscles of the body may assume an "isometric" contraction, wherein the flexing of the muscle results in outward bulge or protrusion thereof. During such an isometric contraction the muscle remains in a substantially static position and/or orientation. In contrast, an "isotonic" contraction of any of a plurality of different muscle bundles results in a movement of the muscle while under tension. This in turn results in a lengthening and shortening of the muscle as the body part with which the muscle is associated moves. An isotonic contraction of a muscle grouping typically occurs when, by way of example only, an individual lifts an object, such that the configuration of the muscle lengthens and shortens depending upon the position of the object being moved.

SUMMARY OF THE INVENTION

The present invention is directed to a method of performing a liposuction procedure and more specifically, a method of utilizing a "liposculpting" technique on a predetermined area of the body. As set forth in greater detail hereinafter, the "treatment area" is generally associated with at least one muscle bundle or a grouping of such muscle bundles, as will be apparent. In performing the subject liposculpting technique, substantially conventional instrumentation may be utilized and a sufficient source of negative pressure be applied to affect a precise removal of unwanted fat tissue from the treatment area.

In addition, the method includes a specific defining of the treatment area from which the fat tissue is to be removed. In at least one preferred embodiment of the present invention, a determination is made of at least a first position of a predetermined muscle bundle, such as when it is in a relaxed state. Cooperatively, the method also includes the determination of at least a second position of the predetermined muscle bundle when it is in a "flexed" or contracted state. The method of the present invention recognizes that certain muscle bundles may be disposed in different flexed or contracted states or positions. By way of example only, the bicep muscle of the arm may assume an "isometric contraction" wherein the muscle is effectively contracted into a flexed orientation resulting in a noticeable outward protrusion or "bulging" thereof. During such an isometric contraction, the flexed muscle maintains a substantially static orientation while the arm assumes the position or orientation to accomplish the flexed position of the muscle.

In contrast, the bicep, as well as other muscle bundles of the human body, may also assume an isotonic contraction or state, wherein the limb or other body part associated with the affected muscle bundle is moving while under tension. As a result, the length and/or other orientation of the affected muscle bundle lengthens and contracts as it passes through the isotonic contraction. A typical example of the bicep of the individual assuming an isotonic contraction is when an object is lifted, substantially at a constant speed. During such an isotonic contraction the affected muscle bundle lengthens and/or contracts during the lifting procedure. Therefore, at least one preferred embodiment of the liposculpting method of the present invention is accomplished by determining a first and second position of the affected muscle bundle when in a relaxed state and in a contracted state, respectively. As set forth above, depending upon the specific muscle bundle under consideration, the third position of the affected muscle bundle may be determined by orienting the affected muscle bundle into an isotonic contraction and determining at least one third position of the muscle when it is so contracted. In contrast, the above-noted second position of the affected muscle bundle is accomplished in a flexed or static orientation thereby defining the affected muscle bundle in an isometric contraction.

As practiced, one preferred embodiment of the liposculpting method of the present invention comprises determining a first position and a second position of the muscle bundle when in a relaxed state and when in a flexed or isometric, contracted state. Determination of each the first and second positions, is accomplished by applying a visual indication, typically in the form of a visual marking, on the skin of the patient or individual under treatment. As such, the first visual indication or first marking occurs when the associated or affected muscle bundle is in a relaxed state and the second indication when the affected muscle bundle is in the flexed or isometric contracted state.

The first and second visual indicators and/or first and second markings will be cooperatively disposed to at least partially define a "treatment area" from which fat tissue is to be removed in a selective manner. A clearly defined muscle bundle having an overall natural appearance for the body area is accomplished when the selective muscle bundle(s) is in either the relaxed position or either of the isometric or isotonic contracted position. Moreover, the various preferred embodiments of the liposculpting method of the present invention are in contrast to the random removal of fat tissue from the defined treatment area. Accordingly, even when carefully and skillfully performed by talented and skilled medical personnel, the random removal of such fat tissue may result in an unnatural, unattractive appearance of the affected body area, as well as the muscle bundle(s) associated therewith.

Therefore, at least one preferred embodiment of the liposculpting method of the present invention comprises the removal of variable quantities of fat tissue from different portions of the treatment area. Such selective and variable fat removal serves to more reliably accomplish a clearly and specifically defined muscle bundle when the muscle bundle is in either a relaxed or contracted state. The removal of variable quantities of fat tissue from different portions of the treatment area can be more specifically defined as removal of different quantities of fat in such a manner that a greater quantity of fat tissue remains in a treatment area in a general direction towards a substantial center of the muscle bundle. Defining the variable quantity of fat tissue to be removed from the treatment area can be further defined the treatment area including a gradually and successively lesser quantity of fat tissue remained therein in a direction away from the center of the muscle bundle.

In practicing the various preferred embodiments of the present invention it is recognized that different muscle bundles will assume at least generally different orientations when in the relaxed state and/or when in the contracted state. By way of example only, the bicep muscle of the arm will be disposed in a substantially static orientation resulting in an outward "bulging" or protrusion, when in the isometric, contracted state. In contrast, the muscle bundles of the abdomen assume a somewhat elongated or "larger" overall configuration when relaxed. However when contracted into a flexed or isometric contracted state, the muscle bundles of the abdomen become somewhat smaller and are collectively disposed in closer relation to one another at least in terms of the center of the abdominal muscle bundles. Therefore, it is recognized that the above noted first and second positions, indicating the associated muscle bundle being either in a relaxed state or a flexed state, may define different orientations, shapes, and locations of the treatment area. As set forth above and described in greater detail hereinafter, the defined treatment area is the portion of the body from which fat tissue is to be removed by suction in selective and variable quantities, depending on the portion of the treatment area being.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As represented in the accompanying drawings, the present invention is directed to a dynamic method 10 of liposculpting different body areas each of which are substantially associated with a predetermined muscle bundle or bundles. As such, application of one or more preferred embodiments of the method 10 of FIG. 1 results in a clearly and specifically defined one or more muscle bundles associated with area of the body being treated. More specifically, at least one embodiment of the method 10 comprises the establishment of the body area to be treated as at 12. As represented in greater detail in the embodiments of FIGS. 2, 3, 4A-4B and 5A-5B, the physical characteristics of various muscle bundles may vary thereby further emphasizing the utility of the liposculpting method of the present invention.

Figure 1:
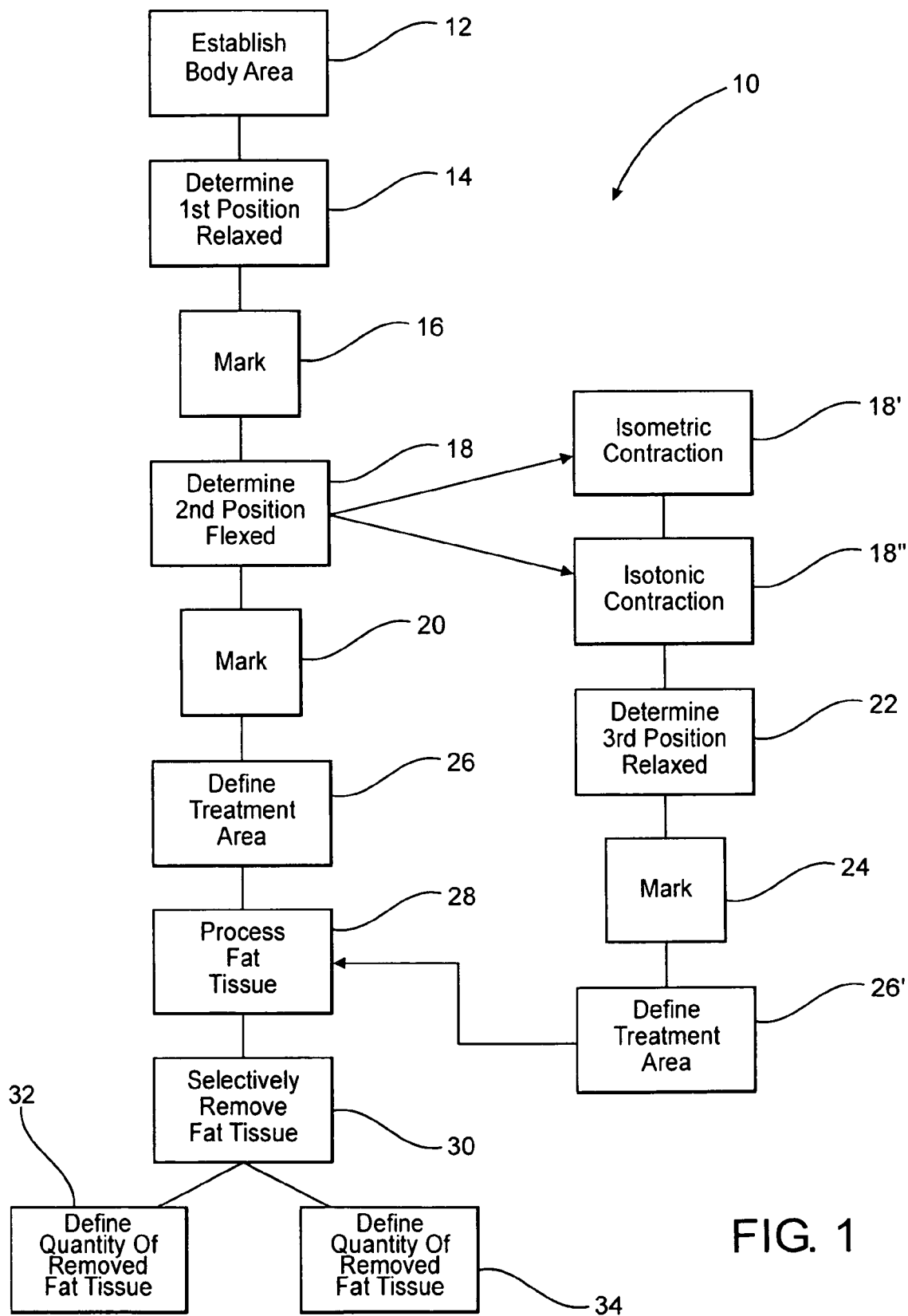
FIG. 1 is a schematic representation in block diagram form of at least one preferred embodiment of the liposculpting method of the present invention.

Again with primary reference to FIG. 1, a specific muscle bundle 100, 102, 103, etc. is first determined for treatment. Subsequently thereafter a first position of the associated muscle bundle is determined when in a relaxed position, as at 14. The first position is therefore clearly indicated, preferably by a visual indication such as a marking 16, and placed on the skin of the patient in overlying and at least partially outlined relation to the associated muscle bundle 100, 102, 103, etc. A second position 18 of the associated muscle bundle is then determined while the muscle bundle is in a flexed state or condition. The second position 18 is provided with an appropriate visual indication such as an additional marking 20. As clearly represented in FIG. 2, both the first position and second position 14 and 18 are respectively represented by the indicated markings 16 and 20.

As will be explained in greater detail hereinafter, at least one preferred embodiment of the present invention defines the contracted or flexed position of the muscle bundle 100 when experiencing an isometric contraction, as at 18'. As recognized, a flexing or isometric state or orientation of the associated muscle bundle 100 occurs when the muscle bundle is in a substantially static orientation. Such an isometric contraction or static orientation of an associated muscle bundle may, by way of example, occur when an individual flexes the bicep and/or other muscles of the arms. As such, the muscle bundle bulges or protrudes outwardly from the body part with which it is associated but maintains a substantially static orientation with little or no movement.

In contrast, the flexed or contracted state of any of the associated muscle bundles 100, 102, 103, etc. may be in the form of an isotonic contraction 18". As also recognized, an isotonic contraction occurs when the muscle bundle is maintained under a given tension but is moving relative to the limb or body part with which it is associated. Further by way of example, the bicep or other muscles of the arm may demonstrate or be oriented in an isotonic contraction when it lifts an object from the floor or other supporting surface. Therefore, at least one additional preferred embodiment comprises the liposculpting method 10 including the determination of a third position 22 and provides a visual indication of such third position 22, such as a marking 24. The third position 22 therefore is directly associated with the orientation of the associated muscle bundle when in an isotonic contraction 18", and may also be used in the determination of the treatment area 26'. Moreover, the treatment areas 26 and 26' may at least partially overlap or otherwise coincide.

Figure 2:
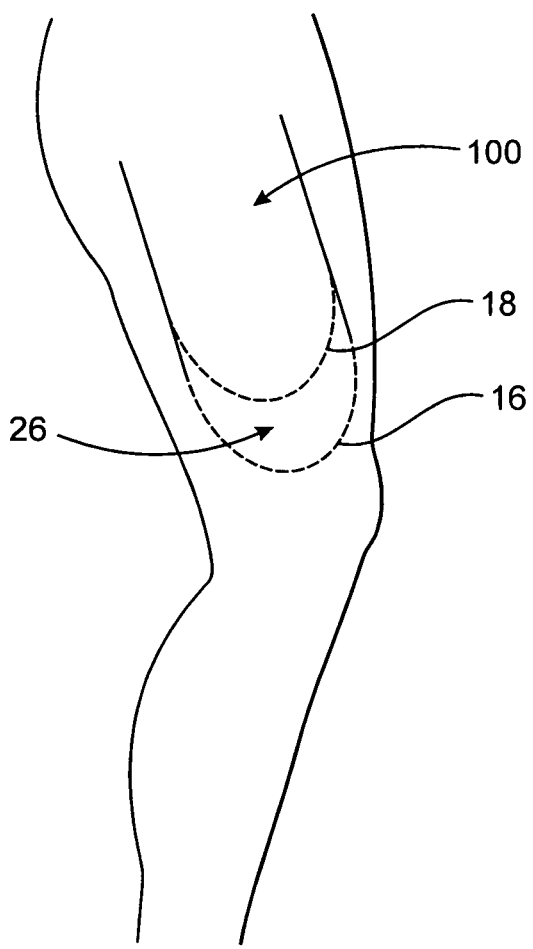
FIG. 2 is a schematic representation of a body area and an associated muscle bundle being treated with the liposculpting method of the present invention.

Therefore, the liposculpting method 10 of the present invention thereby serves to define a treatment area 26, such as when the visual indication 16 and 20 define the first position 14 and the second position 18, respectively, of the associated muscle bundle. The treatment area, as schematically represented in FIG. 2, is indicated as 26 and is defined and/or at least partially established by the disposition of the visual indications or markings 16 and 18 when the associated muscle bundle 100 is in a relaxed state and/or a contracted or flexed state. The treatment area 26 can then be further defined as the body area of the individual or patient from which selected and/or variable quantities of fat tissue is removed by suction utilizing appropriate liposuction instrumentation and/or techniques.

Figure 3:
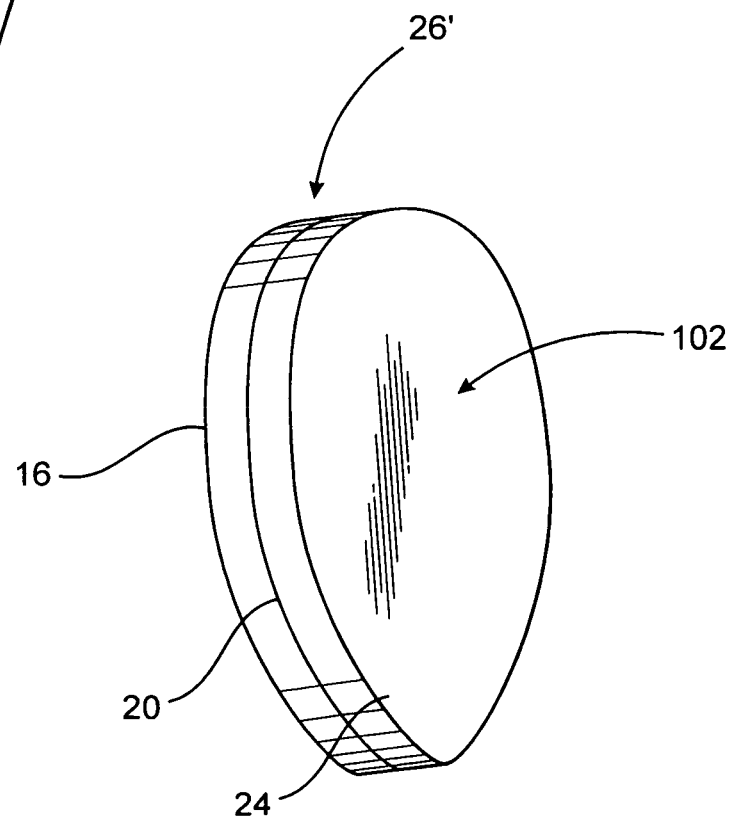
FIG. 3 is a schematic representation of another muscle bundle associated with the liposculpting method of the present invention and further represented as assuming various states of relaxation and/or contraction.

With primary reference to FIGS. 1 and 3, the treatment area 26' may vary or be specifically defined such as when the associated muscle bundle 102 assumes an isotonic contraction as schematically represented. More specifically, the relaxed state of the associated muscle bundle 102 is represented by the visual indication or marking 16. In addition, the orientation of the muscle bundle 102 in a flexed and/or isometric contraction is represented by the visual indications or markings 20. However, when the associated muscle bundle 102 is also oriented in an isotonic contraction as at 18' in FIG. 1, the third position of the muscle 102, when in such an isotonic contraction, is represented by the visual indication or markings 24. As such, the treatment area 26' is thereby defined by the collective disposition of the visual indications or markings 16, 20 and 24. Due to the fact that the isotonic contraction of a given muscle bundle 100, 102, 103, etc. represents the associated muscle bundle being under tension and concurrently moving relative to the limb or body part with which it is associated, the actual visual indication or markings 24 may vary relative to the other markings 16 and 20, as should be apparent.

In either of the above noted preferred embodiments, once the treatment area 26 and/or 26' is defined and established, the fat tissue disposed therein is processed, such as by being fragmented or otherwise prepared to facilitate removal of such fat tissue by suction, as at 28.

Each of the various preferred embodiments of the liposculpting method of the present invention 10 features the removal of selective and/or variable quantities fat tissue from different portions of the treatment area 26 and/or 26', as at 30. As a result, the variable quantities of fat tissue removed from the treatment area may be defined and selectively established by a greater quantity of fat remaining within the treatment area 26 and/or 26' in a direction towards a substantial center of the associated muscle bundle 100, 102, 103, etc, as at 32. Cooperatively, the selective removal of variable quantities of fat tissue from different portions of the treatment area 26 and/or 26' will be further defined as including a gradual and successively lesser quantity of fat remaining within the treatment area 26 or 26' in a direction depending away from the center of the directly associated muscle bundle 100, 102, 103, etc, as at 34.

Figure 4A:
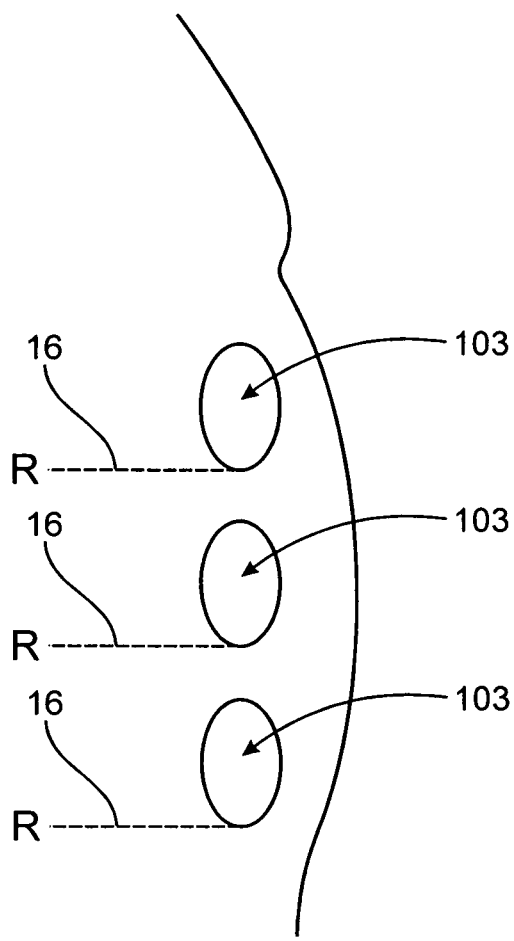
FIGS. 4A and 4B are schematic representations of abdominal muscles representing the body area being treated by the liposculpting method as respectively disposed in a relaxed state and a contracted state.
Figure 4B:
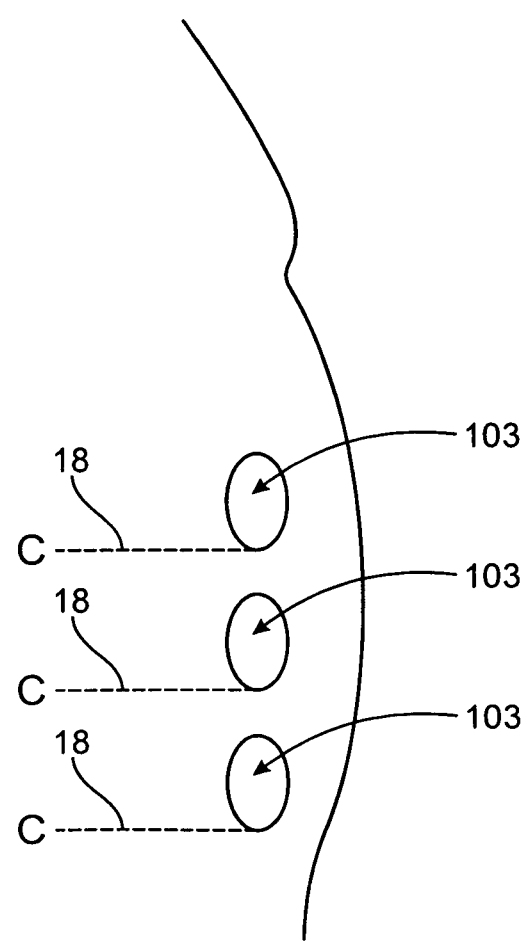
Figure 5A:
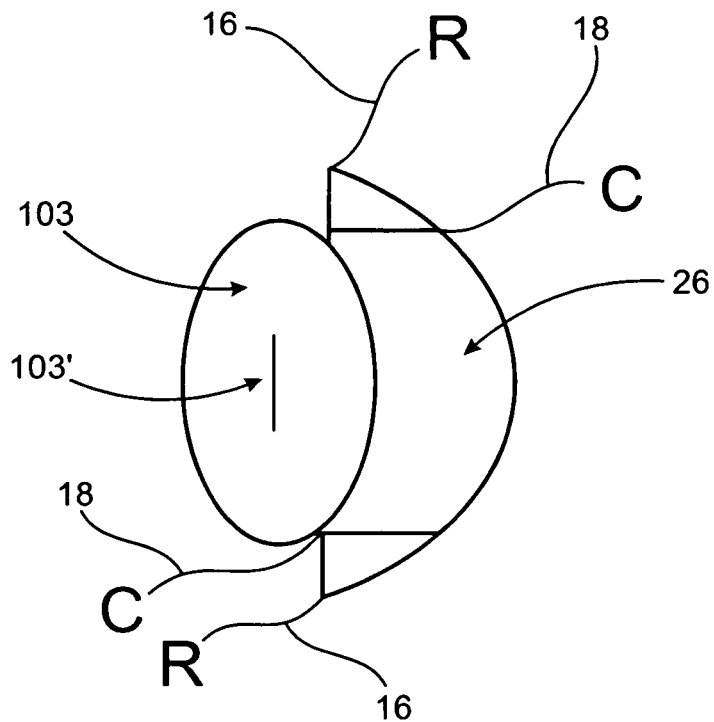
FIGS. 5A and 5B are schematic representations of a single abdominal muscle wherein selective and variable quantities of fat tissue have been removed from different portions of a defined treatment area associated with the represented abdominal muscle.
Figure 5B:
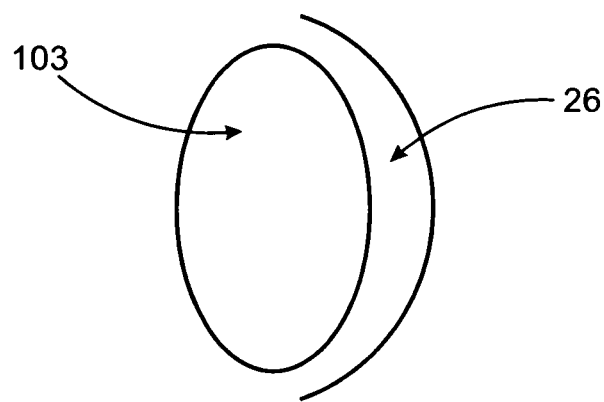

A comparison of FIGS. 2, 3, 4A, 4B, 5A and 5B indicates the different orientations of the muscle bundles 100, 102, 103, etc. By way of example, a thigh or leg muscle as represented in FIG. 2 may be flexed into an isometric contraction wherein the treatment area 26 is defined by the disposition of the visual indications or markings 16 and 18. FIGS. 4A-4B and 5A-5B collectively represent a different muscle bundle or associated muscle bundles in the form of abdominal muscles 103. As represented in FIG. 4A, when the abdominal muscles 103 are in a relaxed state they differ from other muscles, such as in the arms, legs, etc. More specifically, the abdominal muscles 103 tend to elongate or become effectively larger than when in a contracted state, as schematically represented in FIG. 4B. For purposes of clarity, FIGS. 4A and 4B include the visual indications or for appropriate markings 16 and 18, indicating the first and second positions of the muscle bundle(s) when in the relaxed state and/or the flexed state, respectively. With further reference to FIGS. 5A and 5B, the treatment area may thereby be defined by the area disposed in overlying and/or peripheral relation to a single abdominal muscle bundle 103 or the entire bundle of muscle bundles. For purposes of clarity, a single abdominal muscle bundle 103 is being schematically represented in terms of the treatment area 26 and the positioning of the visual indications or markings 16 and 18 when in a relaxed state "R" and a contracted state "C".

As set forth above, once the treatment area 26 or any muscle bundle or bundles 103 is defined and established through the collective disposition of the visual indications or markings 16 or 18, the removal of variable and selective quantities of fat tissue from different portions of the treatment area 26 is conducted, as schematically represented as 30 in FIG. 1. As also more specifically defined, the selective or variable quantity of fat tissue removed from the treatment area 26 can be specifically defined by leaving a greater quantity of fat tissue within the treatment area 26 in a direction towards the substantial center 103' of the associated muscle bundle 103. Removal of selective and variable quantities of fat tissue from the treatment area 26 may be further defined by including a gradual and successively lesser quantity of fat tissue remaining within a portion of the treatment area which is disposed in a direction extending generally away from the center 103' of the muscle bundle 103.

As a result, the liposculpting method 10 of the present invention results in the aforementioned selectively removal of fat quantities from different portions of the treatment area(s) 26 such that instead of having the undesirable, undefined appearance of the associated muscle bundle(s) 103, as represented in FIGS. 4A and 4B, a clearly defined muscle bundle 103 is readily apparent by the establishment of the treatment area having an effective sculpted appearance which corresponds to the directly associated muscle bundle 103 as specifically represented in FIG. 5B.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A method of liposculpting a body area substantially associated with a predetermined muscle bundle, said method comprising:
   determining at least a first position of the muscle bundle when in a relaxed state,
   determining at least a second position of the muscle bundle when in a contracted state,
   defining a predetermined portion of the body as a treatment area,
   defining the boundaries of the treatment area substantially by the disposition of the first and second position of the muscle bundle, and
   removing variable quantities of fat tissue, by suction, from different portions of the treatment area to the extent that a greater quantity of fat tissue remains in a portion of the treatment area closest to a substantial center of the predetermined muscle bundle and a successively lesser quantity of fat tissue remains in a portion of the treatment area extending away from the substantial center of the muscle bundle.

2. A method as recited in claim 1 comprising determining the first position by applying at least a first visual indication to the area of the human body in at least partial alignment with the muscle bundle when in the relaxed state.

3. A method as recited in claim 1, comprising determining at least a third position of the muscle bundle in an isotonic contraction.

4. A method as recited in claim 2 comprising determining the second position by applying at least a second visual indication to the area of the human body in at least partial alignment with the muscle bundle when in a contracted state.

5. A method as recited in claim 4 comprising defining each of the first and second visual indications as markings on the skin of the body area.

6. A method as recited in claim 5 disposing the markings of each of the first and second positions to substantially outline at least a peripheral portion of the muscle bundle when in the relaxed state and when in the contracted state respectively.

7. A method as recited in claim 6 comprising at least defining the boundaries of the treatment area as the outlined periphery of the muscle bundle when in the first position and in the second position.

8. A method as recited in claim 4 disposing the visual indications of each of the first and second position of the muscle bundle to substantially outline at least a portion of a periphery of the muscle bundle when in both the relaxed state and contracted state.

9. A method as recited in claim 8 comprising at least defining the boundaries of the treatment area as the outlined periphery of the muscle bundle when in the first position and when in the second position.

10. A method as recited in claim 4 comprising determining at least a third position of the muscle bundle in an isotonic contraction.

11. A method as recited in claim 10 comprising determining the third position of the muscle bundle by at least a third visual indication to the treatment area by disposing the third visual indication with at least a portion of the muscle bundle when in the isotonic contracted state.

12. A method as recited in claim 11 defining each of the first, second and third visual indications as markings on the skin on the body area.

13. A method as recited in claim 11 disposing said first and second visual indications of each of the first and second positions to substantially outline at least a portion of a periphery of the muscle bundle when in both the relaxed state and the contracted state.

14. A method as recited in claim 13 disposing said third visual indication in cooperative relation to said first and second visual indications to further define boundaries of the treatment area.

15. A method as recited in claim 14 further comprising removing selective quantities of fat tissue by suction to the extent that successively lesser quantities of fat tissue remain in the treatment area extending from the substantial center of the muscle bundle to said third visual indication and from said third visual indication away from the center of the muscle bundle.

16. A method of liposculpting a body area substantially associated with a predetermined muscle bundle, said method comprising:

determining at least a first position and a second position of the muscle bundle when in a flexed position and in a relaxed position respectively, providing at least a first and second visual indication on the body area which are determinative of the first and second positions respectively, defining a treatment area from which fat tissue is to be removed by a disposition of at least the first and second visual indications, processing fat tissue within the treatment area to facilitate removal thereof, removing variable quantities of fat tissue from different portions of the treatment area, defining the variable quantities of fat tissue to include a greater quantity of fat tissue remaining within the treatment area in a direction towards a substantial center of the muscle bundle, and further defining the variable quantities of fat tissue remaining within the treatment area to include a gradual and successively lesser quantity of fat tissue remaining in the treatment area in the direction away from the center of the muscle bundle.

17. A method as recited in claim 16 comprising flexed position as the muscle bundle being in a state of isometric contraction.

18. A method as recited in claim 17 comprising determining at least a third position of the muscle bundle when in a state of isotonic contraction.

19. A method as recited in claim 18, comprising providing at least a third visual indication on the body area which is determinative of the third position, further defining the treatment area by collective disposition of the first, second and third visual indications.

20. A method as recited in claim 16 comprising determining at least a third position of the muscle bundle when in a state of isotonic contraction.

21. A method as recited in claim 20, comprising providing at least a third visual indication on the body area which is determinative of the third position, further defining the treatment area by collective disposition of the first, second and third visual indications.

\* \* \* \* \*